United States Patent [19]

Coulston

[11] Patent Number: 5,270,345
[45] Date of Patent: Dec. 14, 1993

[54] NON-BIOACCUMULABLE PESTICIDES

[75] Inventor: Frederick Coulston, Alamagordo, N. Mex.

[73] Assignee: Coulston International Corporation, Alamagordo, N. Mex.

[21] Appl. No.: 675,924

[22] PCT Filed: Nov. 2, 1989

[86] PCT No.: PCT/US89/04929

§ 371 Date: May 3, 1991

§ 102(e) Date: May 3, 1991

[87] PCT Pub. No.: WO90/04921

PCT Pub. Date: May 17, 1990

Related U.S. Application Data

[63] Continuation-in-part of Ser. No. 268,029, Nov. 4, 1988, abandoned.

[51] Int. Cl.$^5$ .................. A01N 29/04; A01N 31/00; A01N 31/14; A01N 37/34
[52] U.S. Cl. ............................ 514/756; 514/519; 514/715; 514/729; 514/755
[58] Field of Search ............... 514/755, 756, 519, 715, 514/729

[56] References Cited

U.S. PATENT DOCUMENTS

| | | | |
|---|---|---|---|
| 3,062,709 | 11/1962 | Ordas | 514/755 |
| 3,110,648 | 11/1963 | Feichtinger et al. | 514/755 |
| 3,222,249 | 12/1965 | Koremura et al. | 514/755 |

FOREIGN PATENT DOCUMENTS

| | | | |
|---|---|---|---|
| 160039 | 1/1953 | Australia | 514/755 |
| 692546 | 1/1953 | United Kingdom | 514/755 |

Primary Examiner—Allen J. Robinson
Attorney, Agent, or Firm—Leydig, Voit & Mayer, Ltd.

[57] ABSTRACT

Novel pesticidal compositions, which are characterized by biodegradability and do not bioaccumulate to an unacceptable level in fats and tissues of animals, fowl and fish, containing active compounds and optionally a carrier suitable for administering said compounds to a pest by contact, ingestion or inhalation, are disclosed. Such compositions comprise in addition to the carrier compounds of the formula

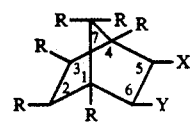

where R is H, Cl or other Hal, hydroxyl, lower alkoxyl, lower alkyl, cyano, $CONR_2$ or $NR_2$ where $R_2$ is H or lower alkyl; X and Y may be R, and when taken together may be —O— or a saturated or unsaturated monocyclic or bicyclic group which may be substituted with R, epoxide, carboxy or carboxymethyl group; and the unsaturated analogs thereof wherein the unsaturation occurs at at least one of the 2 or the 5 positions, and wherein unsaturation may occur optionally in the ring formed by X and Y taken together; with the further proviso that said compound has between 4 and 6 halogens; and a carrier for said compound. Methods of using such pesticides to kill or disable pests are disclosed. Certain novel compounds within the group and novel methods of making said compounds are disclosed.

4 Claims, No Drawings

NON-BIOACCUMULABLE PESTICIDES

This is a continuation-in-part based on application Ser. No. 268,029, filed Nov. 4, 1988 now abandoned.

BACKGROUND OF THE INVENTION

Polychlorinated cyclic hydrocarbons have been known for many years as good insectcides and many of them have been widely used in the past. Such insecticides as DDT, dieldrin, endrin, chlordane, lindane, heptaclor, aldrin, and toxaphene are examples. As the use of these compounds became more widespread and continued for several years, evidence mounted that these compounds were extremely stable to biodegradation and were found to be accumulating in the tissues of animals, birds and fishes, and therefore presumably in man, with toxic effects. As a result, the use of these obviously good insecticides has fallen into disfavor and actually has been banned in many instances. The need for strong pesticides which are not toxic to animals and do not bioaccumulate in the fat and tissues of animals is quite evident and has attracted much attention among researchers, but with very little success.

THE PRIOR ART

As noted above the class of polychlorinated cyclic hydrocarbons is well known in the art and the effect of such compounds on pests is well documented in the literature. It is also known in the art to dechlorinate a polychlorinated hydrocarbon by subjecting it to strong ultraviolet light. Such a process is inefficient because of the large volume of solvents required and the high energy necessary for the generation of a useful ultraviolet light. Yields were low and the cost of the dehalogenated compounds often ran as much as ten times that of the corresponding parent compound.

SUMMARY OF THE INVENTION

This invention relates to a class of novel compositions containing polychlorinated cyclic hydrocarbons having an endomethylene bridged structure, to novel compounds within this group, and to methods of making such compounds. The compounds are characterized generally as being strong or effective pesticides which do not accumulate, or accumulate slowly and not above acceptable limits in the tissues of animals, including man, fishes and fowl. Thus they avoid the environmental problem of bioaccumulation which has eliminated or restricted the use of most polychlorinated pesticides, e.g. Toxaphene, DDT, Dieldrin, Heptaclor, Aldrin and the like.

Bioaccumulation appears to be the ultimate reason for restricting use of highly toxic pesticides, which is caused at least in part by the stability of the compounds, i.e., their resistance to breakdown into less toxic or non-toxic degredation products. Thus, faster biodegredation should result in lower bioaccumulation of the toxic chemicals in cells and tissue of the hosts.

We have found that the relatively non-bioaccumulative compounds of this invention can be made by replacing one or more halogen (chlorine) atoms with a hydrogen on a polyhalogenated cyclic hydrocarbon to make a less halogenated compound which we have found to possess excellent pesticide or repellent activity, usually at least equal to the parent compound in such activity and sometimes even better, but at the same time being less stable to biodegradation and consequently more easily converted into degredation products which are not so environmentally undesirable. The result is an effective pesticide, especially insecticide, which does not bioaccumulate to toxic levels in the host cells or tissue of mammalian species, fowl or fish.

Generally speaking, proton exchange under the influence of ultraviolet light is known as a means of replacing a halogen atom with a hydrogen atom in an organic molecule but the efficiency is known to be low and the product yield is unsatisfactory considering the large amount of energy consumed in the process. We have found a method of increasing the efficiency to acceptable levels, as described in greater detail herein. We have also found other syntheses for making the desired compound which result in good yields, as further described herein.

Certain of the cyclodiene pesticides of this invention may be called dehalogenated (dechlorinated) derivatives of substituted polyhalogenated (polychlorinated) norbornanes, norbornenes or norbornadienes. We prefer however to call them norborphenes or, more simply, bornaphenes. Other inventive compounds are derived from the dimethanonaphthalenes of the class generally represented by aldrin, dieldrin and endrin by dehalogenation to remove one or more halogens adjacent to the double bonds, or by synthesis to achieve the same dehalogenated dimethanonaphthalenes. Such derivatives are characterized by strong pesticide activity while also exhibiting a weakened structure more susceptable to enzymatic or other bio attack which biodegrades the derivative to a form that does not bioaccumulate in tissue to the same degree as the parent compound, or may not accumulate at all.

The novel bornaphenes of this invention are characterized by strong pesticide activity, notably against insects and their larvae but also against agricultural pests (insects) which attack food crops. In general we have found that the new bornaphenes exhibit toxic effects similar to the related more heavily chlorinated compounds from which they may be derived, though sometimes of a somewhat lesser or greater toxic effect. We use the term pest herein to include all of the Phylum Arthropoda, such as the Subphylum Mandibulata, especially the classes Diplopoda, Insecta and Arachnida. Of these are the insects which are most destructive to mammals fish and fowl and to agricultural crops.

When applied in lower concentration these novel compositions act as insect repellents.

Surprisingly we have also found that many of our dehalogenated, non-bioaccumulable derivatives exhibit a knock-down effect against flying insects that is faster and more effective than the more heavily halogenated members, even approaching the knock-down effect of the pyrethrins. The effect is to achieve rapid control and kill of the insect by the combined effect of rapid knock-down plus strong toxicity. Results of certain testing of our compounds is described hereinafter and confirms the combination of pesticidal activity and non-bioaccumulation.

The novel bornaphene pesticides of this invention are characterized as members of the group having the structural formula

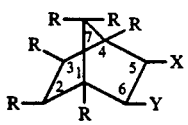

where R is H, Hal (halogen), hydroxyl, alkoxyl, alkyl, amino, dialkylamino, dialkylamido or cyano; X or Y may be the same as R above, or when taken together may be —O— or a saturated or unsaturated monocyclic or bicyclic group which may be substituted with epoxy or an R or carboxy or carboxyalkyl group, and the unsaturated analogs thereof wherein the unsaturation occurs at at least one of the 2 or the 5 positions, and wherein unsaturation may occur in the ring formed by X and Y taken together, with the proviso that said compounds have between 3 and 6 halogens, and preferrably between 4 and 6 halogens. The formula includes the endo and exo isomers of said compounds.

Referring to formula I above, among preferred compounds are those in which X any Y taken together with the basic ring represents a 5 carbon cyclic group which may be saturated or unsaturated and may be substituted with epoxy or an R or carboxy or carboxyalkye group.

Other preferred compounds have at least one chlorine atom at the 7 position and halogen at the 1 and 4 positions, and are characterized by a molecular structure weakened to natural enzyme attack to thereby foster biodegradability and the resultant non-bioaccumulation. Weakening is accomplished by providing hydrogens on the carbon atoms adjacent to the double bonds, as by removing one or more of the chlorines adjacent to the double bonds.

One group of preferred compounds are derivatives of chlordene which, in reference to the structural formula I shown above, have a double bond at the 2 position, less than 6 chlorines and wherein X and Y taken together represent a cyclic group which optionally may be substituted as defined above.

Another group are naphthalenes in which X and Y taken together represent a cyclic group having an endomethylene bridged structure. These compounds are the monodechloro analogs of aldrin and dieldrin, but surprisingly are much more readily biodegradable than the parent compounds.

Still another group are the bicycloheptanes and heptenes in which X or Y is H or Hal or epoxy or lower alkyl.

Synthesis of the Novel Bornaphenes by Ultraviolet Irradiation

The following description sets forth the general procedure which may be adapted readily by those skilled in this art to achieve the desired compounds. We have numbered the compounds for convenience and they will be referred to herein as CIC-numeral or sometimes simply by the numeral.

All chemicals, except CIC-129 and CIC-134, were prepared by irradiation of the parent compound in dilute hexane solution according to the following general procedure:

200 ml n-hexane are aerated with nitrogen for 15 minutes and combined with 2 g of the parent compound. The solution is irradiated with shortwave UV light ($\lambda < 300$ nm) for approximately 90 minutes. The course of the reaction is monitored by gas chromatography (column material OV 101, temperature 200° C., FID-detector). As soon as a composition of about 90–95% of monodechlorinated chemical is observed, the irradiation was terminated and the solvent evaporated. The residue was purified by column chromatography on silica gel (approximately 40 g dry weight silica gel, eluent: hexane). CIC-134 was prepared by extension of the irradiation period. After a composition of 85% of CIC-134 was observed (approximately 12 hours), the irradiation was terminated. The work-up is identical to the general procedure described above.

CIC-129 was prepared by irradiation of bromochlordene (CIC-128) in acetone with long-wave UV light ($\lambda > 300$ nm) for 90 minutes and column chromatography on silica gel (approximately 250 g dry weight silica gel, eluent: hexane, yield 4%).

By following the foregoing procedures we made certain of the compounds listed on Table 1. The parent compound is numbered in our system as an even numbered compound, e.g., CIC-100 or CIC-104 while the dehalogenated new compound is listed usually with the next odd number, e.g., CIC-101, CIC-105, etc. We may list only the dehalogenated compounds with the understanding that the ultraviolet irradiation has replaced one or more halogen with hyrogen. The term "monodechloro" indicates, for instance, that one chlorine atom on the parent compound has been replaced by hydrogen.

TABLE 1

| CIC Code Number, Chemical Name, Molecular Formula and Molecular Weight | | | |
|---|---|---|---|
| CIC Code Number | Chemical Name | Molecular Formula | Molecular Weight |
| CIC-101 | monodechloro-chlordene | $C_{10}H_7Cl_5$ | 304.5 |
| CIC-103 | monodechloro-dihydrochlordene | $C_{10}H_9Cl_5$ | 306.5 |
| CIC-105 | monodechloro-heptachlor | $C_{10}H_6Cl_6$ | 339 |
| CIC-107 | monodechloro-$\beta$-dihydroheptachlor | $C_{10}H_8Cl_6$ | 341 |
| CIC-109 | monodechloro-heptachlorepoxide | $C_{10}H_6Cl_6O$ | 355 |
| CIC-112 | Hydroxychlordene | $C_{10}H_6Cl_6O$ | 355 |
| CIC-113 | monodechloro-hydroxychlordene | $C_{10}H_7Cl_5O$ | 320.5 |
| CIC-114 | Dihydrohydroxychlordene | $C_{10}H_8Cl_6O$ | 357 |
| CIC-115 | monodechloro-dihydrohydroxychlordene | $C_{10}H_9Cl_5O$ | 322.5 |
| CIC-116 | methoxychlordene | $C_{11}H_8Cl_6O$ | 369 |
| CIC-117 | monodechloro-methoxychlordene | $C_{11}H_9Cl_5O$ | 334.5 |
| CIC-118 | nitrilochlordene | $C_{11}H_5Cl_6N$ | 364 |
| CIC-119 | monodechloro-nitrilochlordene | $C_{11}H_6Cl_5N$ | 329.5 |
| CIC-120 | methyl chlordenecarboxylate | $C_{12}H_8Cl_6O_2$ | 397 |
| CIC-121 | methyl monodechloro-chlordenecarboxylate | $C_{12}H_9Cl_5O_2$ | 362.5 |
| CIC-123 | Monodechloro-$\beta$-bromo-dihydrochlordene | $C_{10}H_8Cl_5Br$ | 385.5 |
| CIC-125 | monodechloroaldrin | $C_{12}H_9Cl_5$ | 330.5 |

TABLE 1-continued

CIC Code Number, Chemical Name, Molecular Formula and Molecular Weight

| CIC Code Number | Chemical Name | Molecular Formula | Molecular Weight |
|---|---|---|---|
| CIC-127 | monodechloro-dieldrin | $C_{12}H_9Cl_5O$ | 346.5 |
| CIC-129 | photo-bromochlordene | $C_{10}H_5Cl_6Br$ | 418 |
| CIC-134 | didechloro-β-dihydro heptachlor | $C_{10}H_9Cl_5$ | 306.5 |
| CIC-135 | didechloroisodrin | | |
| CIC-136 | monodechloroendrin | $C_{12}H_9Cl_5O$ | 346.5 |
| CIC-137 | 1,2,4,7,7-pentachloronorborna-2,5-diene | | |
| CIC-138 | 1,2,4,6-endo,7,7-hexachloronornorn-2-ene | | |
| CIC-139 | 1,2,4,5-endo,7,7-hexachloronornorn-2-ene | | |
| CIC-140 | monodechloroisodrin | | |
| CIC-141 | 1,2-endo,4,7,7-pentachloronorbornane | | |
| CIC-142 | 1,4,7,7-tetrachloronorbon-2-ene | | |
| CIC-143 | 1,2,3,4,5-endo,6-endo,7-syn-heptachoronorborn-2-ene | | |
| CIC-144 | 1,2-endo,3-endo,4,7-syn-pentachlorononorbornane | | |
| CIC-145 | 1,2-endo,3-endo,4-tetrachloronorbornane | | |
| CIC-146 | 1,2-exo,3-endo,4,7,7-hexachloronorbornane | | |
| CIC-147 | 1,2,4,7,7-pentachloronorborn-2-ene | | |
| CIC-148 | 1,2-endo,3-endo,4,7-anti-pentachlronorbornane | | |
| CIC-149 | 1,4,7,7-tetrachloronorbornan-2,3-endo-epoxide | | |
| CIC-150 | 1,4,7,7-tetrachloronorbornan-2,3-exo-epoxide | | |
| CIC-151 | 1,4,7,7-tetrachloro-2-methyl-norbornane | | |
| CIC-152 | 1,4,5-endo,7,7-pentachloronorborn-2-ene | | |
| CIC-154 | 1,4,7,7-tetrachloro-norbornan-diene | | |
| CIC-155 | 1,2-endo,3-endo,4,5,6-hexachloronorborn-2-ene | | |
| CIC-156 | 1,2-exo,3-exo,4,5,6-hexachloronorborn-2-ene | | |
| CIC-158 | mixture of CIC 143, 144, 145 and 148 (see Example 2) | | |
| CIC-160 | endo-tricyclo $(7,2,1,^{2,8})$ dodecadien (6,10) | | |
| CIC-164 | nitrilochlodane | $C_{11}H_7Cl_6N$ | |
| CIC-165 | azaaldrin | $C_{11}H_8Cl_5N$ | |
| CIC-168 | azadieldrin | $C_{11}H_8Cl_5NO$ | |

TABLE 2

Valuable compounds are listed below in reference to the structural formula (an unfulfilled valence in a saturated compound signifies presence of hydrogen).

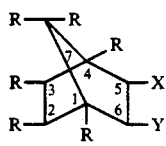

| COMPOUND CIC- | VALUE OF R IN POSITION NUMBER =* | | | | | X 5 | Y 6 |
|---|---|---|---|---|---|---|---|
| | 1 | 2 | 3 | 4 | 7 | | |
| 101 | Cl | ** | Cl | Cl | 2Cl | 2 | 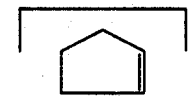 |
| 103 | Cl | | Cl | Cl | 2Cl | 2 | 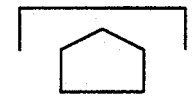 |
| 105 | Cl | | Cl | Cl | 2Cl | 2 | 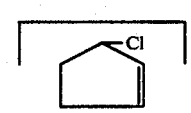 |
| 107 | Cl | | Cl | Cl | 2Cl | 2 | 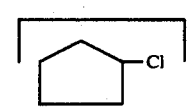 |
| 109 | Cl | | Cl | Cl | 2Cl | 2 | 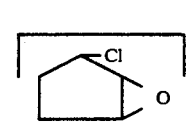 |

TABLE 2-continued

Valuable compounds are listed below in reference to the structural formula (an unfulfilled valence in a saturated compound signifies presence of hydrogen).

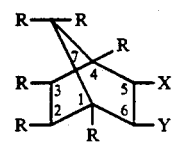

| COMPOUND CIC- | VALUE OF R IN POSITION NUMBER =* | | | | | X 5 | Y 6 |
|---|---|---|---|---|---|---|---|
| | 1 | 2 | 3 | 4 | 7 | | |
| 112 | Cl | Cl | Cl | Cl | 2Cl | 2 | 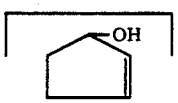 |
| 113 | Cl | | Cl | Cl | 2Cl | 2 | 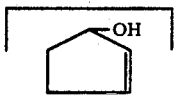 |
| 114 | Cl | Cl | Cl | Cl | 2Cl | 2 | 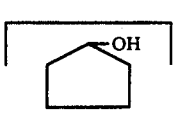 |
| 115 | Cl | | Cl | Cl | 2Cl | 2 | 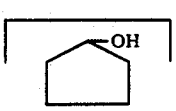 |
| 116 | Cl | Cl | Cl | Cl | 2Cl | 2 | 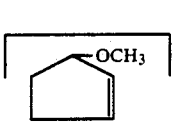 |

TABLE 2-continued

Valuable compounds are listed below in reference to the structural formula (an unfulfilled valence in a saturated compound signifies presence of hydrogen).

| COMPOUND CIC- | VALUE OF R IN POSITION NUMBER =* | | | | | X | Y |
|---|---|---|---|---|---|---|---|
| | 1 | 2 | 3 | 4 | 7 | 5 | 6 |
| 117 | Cl | | Cl | Cl | 2Cl | 2 | (cyclopentene-OCH₃) |
| 118 | Cl | Cl | Cl | Cl | 2Cl | | (cyclopentene-CN) |
| 119 | Cl | | Cl | Cl | 2Cl | 2 | (cyclopentene-CN) |
| 121 | Cl | | Cl | Cl | 2Cl | 2 | (cyclopentene-COOCH₃) |
| 123 | Cl | | Cl | Cl | 2Cl | 2 | (cyclopentene-Br) |
| 127 | Cl | | Cl | Cl | 2Cl | 2 | (norbornene-O) |
| 134 | Cl | | | Cl | 2Cl | 2 | (cyclopentene-Cl) |
| 135 | Cl | | | Cl | 2Cl | 2 | (norbornene) |
| 136 | Cl | | Cl | Cl | 2Cl | 2 | (norbornene-O) |
| 137 | Cl | | Cl | Cl | 2Cl | 2,5 | |
| 138 | Cl | Cl | | Cl | 2Cl | 2 | Cl |
| 139 | Cl | Cl | | Cl | 2Cl | Cl | |
| 140 | Cl | | Cl | Cl | 2Cl | | (norbornadiene) |
| 141 | Cl | Cl | | Cl | 2Cl | | |
| 142 | Cl | | | Cl | 2Cl | 2 | |
| 144 | Cl | Cl | Cl | Cl | Cl | | |
| 145 | Cl | Cl | Cl | Cl | | | |
| 146 | Cl | Cl | Cl | Cl | 2Cl | | |
| 147 | Cl | Cl | | Cl | 2Cl | 2 | |
| 148 | Cl | Cl | Cl | Cl | Cl | | |
| 149 | Cl | | | Cl | 2Cl | | (>O endo) |
| 150 | Cl | | | Cl | 2Cl | | (>O exo) |
| 151 | Cl | CH₃ | | Cl | 2Cl | | |
| 152 | Cl | | | Cl | 2Cl | 2 | Cl |
| 154 | Cl | | | Cl | 2Cl | 2,5 | |
| 155 | Cl | Cl endo | Cl endo | Cl | | 2 | Cl | Cl |
| 156 | Cl | Cl exo | Cl exo | Cl | | 2 | Cl | Cl |
| 164 | Cl | Cl | Cl | Cl | 2Cl | 2 | (cyclopentene-CN) |

*"=" means double bond at position number.
**a blank space means H at that position.

SPECIFIC EMBODIMENTS

Example I

Preparation of 1,2,3,4,5-endo,6-endo-7,7-Octa-chloronorborn-2-ene

A solution of 25 g of hexachlorocyclopentadiene in 49 g of 1,2-dichloroethylene (80% trans, 20% cis) is heated in a autoclave at 190° for 4 h in a Diels-Alder reaction. By GC analysis the two major products are in the ratio 3.1. The reaction is repeated, and the two mixtures are worked up together.

Dichloroethylene is stripped out, and the dark brown residue is chromatographed on silica gel (ca.650 g) with petroleum ether. The first product eluted is an unidentified compound $C_7H_2Cl_8$. The more polar product and the one in greater yield is ca. 29 g of the desired cis-endo Diels-Alder adduct. It is crystalline, but dark brown. The color can be removed by sublimation.

$^{13}$C-NMR: $\delta$(CDCl$_3$) 132.36 (s), 99.07 (s), 82.51 (s), 64.69 (d).

GCMS m/e 366 (m+, $C_7H_2Cl_8$).

$^1$H-NMR: $\delta$(CDCl$_3$) 4.97 (s).

Example 2

Preparation of 1,2,3,4,5-endo,6-endo,7-syn-Heptachloronorborn-2-ene (CIC-143), 1,2-endo,3-endo, 4,7-syn -Pentachloronorbornane (CIC-144), 1,2-endo, 3-endo, 4-Tetra-chloronorbornane (CIC-145), and 1,2-endo, 3-endo, 4,7-anti- Pentachloronorbornane (CIC-148)

A slurry of 50 g sodium acetate ( 3H$_2$O) and 3.00 g of 10% Pd on charcoal is stirred in 100 ml of 2-propanol under hydrogen for 20 min. A solution of 1,2,3,4,5-endo,6-endo-7,7-octachloronorborn-2-ene (19.0 g) in 300 ml of 2-propnol is added. Over 1 h 40 min. 8900 ml of hydrogen is absorbed. The mixture is filtered, while care is taken to maintain an atmosphere of nitrogen over it. The flask and filtered solids are washed with dichloromethane. The solvent is distilled out on a rotary evaporator. Since the distillate contains some product, it is diluted with water and extracted with petroleum ether. This product, now designated CIC-158, when so made, has an average molecular weight not greater than 300 and may be used as a pesticide without further separation or purification. At this molecular weight the product is biodegradable and does not bioaccumulate to an undersirable degree in animal fats and tissues.

This combined product was chromatographed on silica gel with petroleum ether. The fractional products, in order of elution, are compound 144 (5 g, 19%), compound 145 (7 g, 30%), compound 148 (4 g, 15%) and compound 143 (4 g, 12%).

| $^{13}$C-NMR: $\delta$(CDCl$_3$) | | | |
|---|---|---|---|
| 143: | 131.03 (s), | 78.12 (s), | 77.02 (d), | 65.12 (d). |
| 144: | 72.0 (d), | 70.7 (s), | 64.9 (d), | 30.1 (t). |
| 145: | 67.8 (s), | 66.9 (d), | 51.6 (t), | 32.7 (t). |
| 148: | 72.1 (s), | 70.2 (d), | 64.4 (d), | 30.1 (t). |
| GCMS m/e (m+) | | | |
| 143: | 332 ($C_7H_3Cl_7$) | | |
| 144: | 266 ($C_7H_7Cl_5$) | | |
| 145: | 232 ($C_7H_8Cl_4$) | | |
| 148: | 266 ($C_7H_7Cl_5$) | | |

| | 143 | | 144 | | 145 | | 148 | |
|---|---|---|---|---|---|---|---|---|
| | Found | Calc. | Found | Calc. | Found | Calc. | Found | Calc. |
| C | 25.07 | 25.08 | 31.46 | 31.33 | 35.91 | 35.94 | 31.28 | 31.33 |
| H | 0.98 | 0.90 | 2.72 | 2.63 | 3.48 | 3.45 | 2.62 | 2.63 |
| Cl | 73.9 | 74.02 | 66.0 | 66.05 | 60.4 | 60.62 | 66.0 | 66.05 |

Example 3

Preparation of 1,2-endo,4,7,7-Pentachlor-norbornane (CIC-141)

Sodium acetate (225 g with three molecules of water of hydration) and 9.0 g of 10% palladium on charcoal are stirred in 750 ml of methanol under hydrogen overnight. To this is added 100 g of 1,2,3,4,5-endo,7,7-heptachloronorborn-2-ene, prepared by the reaction of hexachlorocyclopentadiene with vinyl chloride. Over 8 h ca. 23 liters of hydrogen are absorbed. On further stirring overnight about another liter is absorbed. Under reduced pressure the methanol is removed. The product is taken into dichloromethane and filtered through about a liter of silica gel. Stripping out the CH$_2$Cl$_2$ leaves a dark brown, pasty mass, which still contains some acetic acid. A second filtration column, with petroleum ether, removes the color and the acetic acid. Stripping the solvent yields 72 g (ca. 90% of theory) of 141 (84% pure). The product can be recrystallized from petroleum ether.

$^{13}$C-NMR: 97.8 (s), 76.5 (s), 71.5 (s), 61.3 (d), 47.0 (t), 35.8 (t) 30.3 (t).

| Analyses | Found | Calc. for $C_7H_7Cl_5$, MW 268.4 |
|---|---|---|
| C | 31.51 | 31.32 |
| H | 2.66 | 2.63 |
| Cl | 66.0 | 66.05 |

Example 4

Preparation of 1,4,7,7-Tetrachloronorborn-2-ene (CIC-142)

A slurry of KOH powder in a solution of 36.1 g of 1,2-endo,4,7,7-Pentachloronorbornane (141) in 104 g of tert-butanol is stirred for 37 hours under reflux. The total amount of KOH added is 40 g. By GC only 1% of the starting material remains. The mixture is partitioned between water and petroleum ether, each of which is backwashed. The combined petroleum ether phases are dried over Na$_2$SO$_4$ and stripped to yield 30.7 g crude 142. Recrystallization from petroleum ether gives 26.0 g (83% of theory) of 142 (>99% pure). [S.: D. I. Davies and P. J. Rowley, J. Chem. Soc. (C), 424 (1969); different method]

$^{13}$C-NMR $\delta$(CDCl$_3$) 136.3, 104.7, 76.1, 34.1.

| Analyses | Found | Calc. for $C_7H_6Cl_4$, MW 231.96 |
|---|---|---|
| C | 36.22 | 36.24 |
| H | 2.59 | 2.61 |
| Cl | 60.9 | 61.15 |

Example 5

Preparation of 1,2-exo,3-endo,4,7,7-Hexachloronorbornane (CIC-146)

A solution several grams of 1,4,7,7-tetrachloronorborn-2-ene (142) (ca. 85% pure) in ca. 25 ml CCl$_4$ is saturated with Cl$_2$ and exposed to sunlight for an hour, resaturated with Cl$_2$ and exposed for a second time to sunlight. GC indicates a nearly quantitative reaction. The solvent is removed to leave an oil that slowly crystallizes. It is recrystallized from warm hexane. The crystals are very pure trans addition product 146. More pure product can be obtained from the mother liquor by column chromatography.

$^{13}$C-NMR; $\delta$(CDCl$_3$) 95.76 (s), 75.37 (s), 74.05 (s), 70.67 (d), 68.17 (d), 36.74 (t), 29.54 (t).

| Analyses | Found | Calc. for $C_7H_6Cl_6$, MW 302.8 |
|---|---|---|
| C | 27.69 | 27.76 |
| H | 2.04 | 2.00 |
| Cl | 70.2 | 70.24 |

Example 6

Preparation of 1,2,4,7,7-Pentachloronorborn-2ene (CIC-147)

1,2-exo,3-endo,4,7,7-Hexachloronorbornane (146) (1.2 g) is dissolved in 30 ml tert-butanol. Powdered KOH (5.0 g) is added, and the mixture is heated under reflux for 6.5 h. After partition between water and petroleum ether and backwashing the organic phase is dried over $Na_2SO_4$ and stripped of solvent to yield an amorphous solid. This is recrystallized three times from hexane chilled in dry ice. The product is 97% pure 147 (57% of theory). [S. Schulte-Hostede, S. Gäb and F. Korte, Chem. Ber. 111, 2646 (1978); different method]

$^{13}$C-NMR: $\delta(CDCl_3)$ 136.7, 130.7, 103.1, 79.7, 75.4, 35.6, 33.6.

GCMS: m/e (M+) 264 ($C_7H_5Cl_5$); base peak 229 (m+-Cl).

Example 7

Preparation of 1,4,7,7-Tetrachloronorbornan-2,3-endo-epoxide (CIC-149) and 1,4,7,7-Tetrachloronorbornan-2,3-exo-epoxide (CIC-150)

To a solution of 36 g $CrO_3$ in 100 ml glacial acetic acid are added in one step 12.0 g of 1,4,7,7-tetrachloronorborn-2-ene. In spite of ice-water cooling there is a rapid exotherm to 80°. Acetic acid (50 ml) is added for cooling, and the exotherm stops quickly. The solution is warmed back up to 73° over half an hour. The mixture is poured into water and extracted with petroleum ether. The organic phase is dried over $Na_2SO_4$ and stripped to 2.6 g (Most of the product is an unidentified material not extracted from the water/acetic acid layer even with dichloromethane). The two epoxides are separated by chromatography on silica gel with increasing amounts of chloroform in petroleum ether. Epoxide fractions were recrystallized and sublimed at 70°-90° C./15 mm Hg for analysis. Yield, ca. 5% of each epoxide.

| $^{13}$C-NMR: $\delta(CDCl_3)$ | (less polar epoxide) | 104.12 (s), 71.96 (s), 62.20 (d), 31.86 (t). |
|---|---|---|
| | (more polar epoxide) | 92.26, 72.61, 55.33, 35.35. |

| Analyses | 149 (less polar epoxide) | 150 (more polar epoxide) | calc. for $C_7H_6Cl_4O$ |
|---|---|---|---|
| C | 33.87 | 33.88 | 33.91 |
| H | 2.49 | 2.43 | 2.44 |
| Cl | 57.1 | 57.1 | 57.20 |

Example 8

Preparation of 1,2,4,6-endo,7,7-Hexachloronorborn-2-ene (CIC-138) and 1,2,4,5-endo,7,7-Hexachloronorborn-2-ene (CIC-139)

1,2,3,4,5-endo,-7,7-Heptachloronorborn-2-ene (lit.) (25 g) is irradiated in 200 ml of hexane with a UV lamp (philips HPK125W) through a water-cooled quartz cooling finger. A grown film is deposited slowly on the quartz and is removed with $CH_2Cl_2$ about every four hours.

After 22 hours the conversion to a ca. 1:1 mixture of the isomeric double-bond-monodechlorinated isomer 138 (more polar) and 139 (less polar) is about 96%, as determined by GC.

The mixture may be irradiated further to produce the double-bond-didechlorinated compound CIC-152.

Alternatively, the isomers can be separated by chromatography with petroleum ether on a silica gel column; both are colorless, crystalline compounds after recrystallization from cold petroleum ether.

| $^{13}$C-NMR: $\delta(CDCl)$ |
|---|
| 138: 136.3 (s), 131.7 (d) 102.4 (s), 83.5 (s), 73.9 (s), 60.1 (d), 45.6 (t). |
| 139: 138.2 (s), 129.1 (d), 101.6 (s), 79.4 (s), 78.8 (s), 61.9 (d), 45.1 (t) |

| Analyses | Found 138 | Found 139 | Calc. for $C_7H_4Cl_6$, Mw 300.86 |
|---|---|---|---|
| C | 27.85 | 27.86 | 27.84 |
| H | 1.32 | 1.30 | 1.34 |
| Cl | 70.0 | 69.8 | 70.72 |

Example 9

Preparation of 1,4,5-endo,7,7-Pentachloronorborn-2-ene (CIC-152)

Pure 1,2,3,4,5-endo,7,7-heptachloronorborn-2-ene (1.0 g) in 180 ml of hexane is irradiated through quartz with a UV light (Philips HPK125W) for four hours. By GC the product is mostly the double-dond-didechlorinated compound. Eight such reactions are combined, chromatographed on silica gel with petroleum ether, and recrystallized from the same solvent. The yield is 2.2 g (>95% by GC; 33% yield).

$^{13}$C-NMR: $\delta(d_6\text{-Acetone})$ 137.8, 135.0, 103.6, 80.4, 75.4, 60.98, 45.54.

$^1$H-NMR $\delta(CDCl_3)$ 6.36 (br d, J=6 4 Hz), 6.18 (dt, J=6 4, 0.7 Hz), 4.65 (ddd, J=8.2, 3.2, 0.6 Hz), 3.05 (ddd, J=13.1, 8.2, 0.5 Hz), 2.14 (dd, J=13.1, 3.0 Hz).

| Analyses | Found | Calc. for $C_7H_5Cl_5$, MW 266.41 |
|---|---|---|
| C | 31.49 | 31.56 |
| H | 1.94 | 1.89 |
| Cl | 66.1 | 66.55 |

Example 10

Preparation of 1,2,4,7,7-Pentachloronorborna-2,5-diene (CIC-137)

The crude monodechlorinated isomers CIC-138 and CIC-139 from 25 g of 1,2,3,4,5-endo,7,7-heptachloronorborn-2-ene 157 are stripped of solvent on a rotary evaporator and redissolved in 100 g tert-butanol. Powered KOH (18 g) is added, and the mixture is heated for four hours at 85°-95° in a round-bottomed flask equipped with a heavy magnetic stirrer and a reflux condensor. More KOH is added at intervals during the reaction (to a total of 38 g). The mixture is partitioned between water and petroleum ether. Each phase is back-extracted; the combined organic phases are dried over $Na_2CO_3$ and stripped on a rotary evaporator to 22.5 g of brown crystals (over 100%, but not at all pure). This crude product can be recrystallized from petroleum ether. The compound decomposes over several days at room temperature. M.p. 79°-81° ($CHCl_3$).

$^{13}$C-NMR: $\delta(CDCl_3)$ 145.4 (s), 142.1 (d), 140.5 (d), 134.0 (d), 118.0 (s), 84.5 (s), 80.0 (s).

| Analyses | Found | Calc. for $C_7H_3Cl_5$, MW 264.39 |
|---|---|---|
| C | 31.96 | 31.79 |
| H | 1.17 | 1.14 |
| Cl | 65.5 | 67.06 |

Example 11

Preparation of 1,4,7,7-Tetrachloronorbornadiene.

A slurry of 25 g of powered KOH in a solution of 13 g of 1,4,5-endo,7,7-pentachloronorborn-2-ene (CIC-152) in 50 ml of tert-butanol is heated under reflux for seven hours, at which time GC analysis indicates full conversion of 152.

The mixture is partitioned between water and petroleum ether. After back-washing of both phases, the combined petroleum ether phases are dried over Na$_2$SO$_4$ and stripped of solvent to yield 10.9 g of crude 1,4,7,7-tetrachloronorbornadiene (97%). The product is recrystallized from petroleum ether. It decomposes over several days at room temperature.

$^{13}$C-NMR: δ(CDCl$_3$) 142.0, 119.9, 81.4.
$^1$H-NMR: δ(CDCl$_3$) 6.65 (s).

| Anaylses | Found | Cal. for C$_7$H$_4$Cl$_4$, MW 229.94 |
|---|---|---|
| C | 36.53 | 36.56 |
| H | 1.80 | 1.75 |
| Cl | 61.1 | 61.69 |

GCMS: m/e (m+) 228 (C$_7$H$_4$Cl$_4$).

Example 12

Preparation of Monodechloro-Isodrin (CIC-140)

1,2,4,7,7-Pentachloronorborna-2,5-diene (137) (660 mg) and cyclopentdiene (240 g) are sealed in a glass ampoule and heated at 160°–170° for 1.5 h. The mixture becomes black; after filtration through a short silica-gel column it is chromatographed on a silica-gel column with petroleum ether. The yield of crude product (140) is 520 mg. (63%). Recrystallization from petroleum ether gives 370 mg (45%).

$^{13}$C-NMR: δ(CDCl$_{13}$) 134.4, 130.4, 130.1, 127.8, 108.0, 81.2, 77.0, 54.6, 53.6, 49.2, 43.7 (2C).
GCMS: m/e (M+) 328 (C$_{12}$H$_9$Cl$_5$).

| Analyses | Found | Calc. for C$_{12}$H$_9$Cl$_5$, MW 330.49 |
|---|---|---|
| C | 43.65 | 43.61 |
| H | 2.77 | 2.74 |
| Cl | 52.7 | 53.65 |

Example 13

Preparation of Monodechloroendrin (CIC-136)

A solution of 3.13 g of monodechloroisodrin (140) and 1.4 g 40% peracetic acid in 25 ml benzene is allowed to stand for ca. 4.5 h at room temperature. Another 1.4 g 40% peracetic acid is added. After a total of 9 h GC shows ca. 7% starting material remaining. The solution is extracted with aqueous NaHCO$_3$, dried over Na$_2$SO$_4$, and concentrated. Crystals of epoxide (136) form and are filtered. By GC they are 91% pure.

$^{13}$C-NM: δ(CDCl$_3$) 135.72 (s), 132.17 (d), 109.54 (s), 80.35 (s), 76.40 (s), 54.78 (d), 54.42 (d), 50.87 (d), 47.46 (d), 39.77 (d), 39.28 (d), 30.86 (t).

| Analyses | Found | Calc. for C$_{12}$H$_9$Cl$_5$O |
|---|---|---|
| C | 41.47 | 41.61 |
| H | 2.63 | 2.60 |
| Cl | 50.9 | 51.17 |
| O | 4.56 | 4.62 |

Example 14

Preparation of Didechloroisodrin (CIC-135)

A solution of 8 g of 1,4,7,7-tetrachloronorbornadiene and cyclopentadiene (added at intervals to a total of 7 g) in 10 ml of toluene is heated under reflux for 17 hours. After removal of the solvent under vacuum the residual dark brown mass is chromatographed on silica gel with chloroform. The yield of 135 is 5.8 g after recrystallization from warm CH$_2$Cl$_2$. M.p. 126°–128°.

A second component with the same empirical formula is to be found in the mother liquor. This is apparently the 2+2 cycloaddition product from 135.

$^{13}$C-NMR: δ(CDCl$_3$) 132.7, 132.2, 109.1, 78.4, 53.8, 50.1, 44.2.

| Analyses | Found | Calc. for C$_{12}$H$_{10}$Cl$_4$, MW 296.00 |
|---|---|---|
| C | 48.42 | 48.70 |
| H | 3.36 | 3.38 |
| Cl | 48.0 | 47.92 |

Example 15

Preparation of 1,4,7,7-Tetrachloro-2-methyl-norbornane (CIC- 151)

Bromadan (5-Bromomethyl-1,2,3,4,7,7- hexachloronorborn-2-ene) is reacted with hydrogen and a 10% palladuim in methanol catalyst with almost quantitative (>90%) yield of 1,4,7,7- Tetrachlor -2-methyl-norbornane, which is a powerful pesticide but also readily biodegradable and not accmulated in animal tissue to an undesirable degree. It is notable that, in a single reaction, we remove the bromine and also 2 chlorines at 2 and 3 positions, while saturating the double bond at 2, all without affecting the chlorines in the 7 position. The compound is biodegradable and non-accumulable and one possible explanation is that the single bond at the 2-3 position is unstable and weak because the chlorine at 1 position attracts the electron from the 2 or 3 hydrogen.

Other compounds similar to 1,4,7,7-Tetrachloro-2-methyl-norbornane may be made to increase or decrease the stability to biodegradation, the polarity, the pesticidal activity and the toxicity of this group; as by other members of the lower alkyl group than methyl, adding a more polar group such as hydroxyl or lower alkoxyl.

Example 16

By known methods, starting with hexachlorocyclopentadiene is made the compound 1,1,2,3,4,4-Hexachlorocyclopent-2-ene which is converted in good yield (85%) by reaction with calcium in tertiary butanol to dehydro 1,2,3,5,5- Pentachlorocyclopentadiene.

By further reaction of the above compound in a Diels-Alder reaction with vinylchloride in 50% yield is obtained

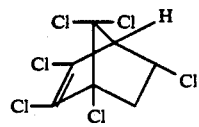

Said compound is further reacted with potassium hydroxide in tertiary butanol to achieve the dechloro analog in which chlorine in the 5 position is removed and a double bond at 5 is substituted. That compound is reacted in a Diels-Alder reaction in 60% yield with cyclopentadiene to achieve a monodechloro derivative of Isodrin which is a strong pesticide but also readily biodegradable.

Example 17

Preparation of 1,2-endo,3-endo,4,7-synpentachloronorbornane (CIC-144)

Hexachlorocyclopentadiene was hydrogenated by known method to pentachlorocyclopentadiene which was subjected to a Diels-Alder reaction with (cis) dichloroethylene for about 5 hours at 175°–180° C. to achieve a good yield (about 60%) of 1,2-endo,3-endo, 4,5,6,7-synheptachloronorborn-2-ene. This product was hydrogenated over a Palladium on charcoal catalyst in methanol-sodium acetate solution in about 90% yield to 1,2-endo,3-endo,4,7-syn-pentachloronorbornane (CIC-144).

Tests to Confirm Insecticidal Activity

Tests established that the novel cyclodiene derivatives of this invention are effective pesticides and repellents against a wide variety of species of arthropods and arachnids (primarily blood sucking insects such as mosquitoes, biting flies and non-insects such as ticks), aphids, ants, hornets, and the like, and also their larvae, as well as against agricultural pests.

To demonstrate the insecticidal activity we chose a test against mosquitoes (*Aedes aegypti*) as disclosed herein. We also tested the compounds for toxicity to animals, using the rat as a typical species, and we disclose the results herein.

The experimental design of the test for activity against mosquitoes is as follows.

One ml of a one percent (1.0%) solution of the chemical in acetone was applied to a piece of filter paper by means of syringe and the acetone allowed to evaporate. The filter paper was then placed in a petri dish and 10–20 mosquitoes (*Aedes aegypti*) added. The effect of the chemical on the mosquitoes (flying activity, mortality) was observed and recorded for up to 72 hours. Generally the experiments were in triplicate, the parent cyclodiene and its dechlorinated derivative were tested and compared to the control; the filter paper of the control was treated with acetone only. A total of 9 pairs of chemicals (parent cyclodiene and dechlorinated derivative) and CIC-134 were tested according to the procedure above. The results are indicated in Table 3.

The same series of experiments was performed with lower concentrations of the test material, i.e. at 0.5% and 0.125% in acetone. These tests showed the same general findings as the experiments at 1% concentration.

The monodechlorinated derivatives (odd CIC numbers) generally show a faster activity than the corresponding parent compounds (next lower even CIC number). The most striking difference observed was between CIC-106 (λ-dihydroheptachlor) and its dechlorinated derivative CIC-107 (monodechloro- β-dihydroheptachlor). Whereas CIC-107 at 1% concentration killed all the mosquitoes within 4 hours, the same experiment lasted 24 hours with CIC-106. A similarly striking difference was observed between CIC-116 and CIC-117. The periods of time necessary to kill all the mosquitoes were: CIC-116 (methoxychlordene), 12 hours; CIC-117 (monodechloromethoxychlordene), 5.75 hours. In 5 of the remaining 7 pairs the monodechloro derivative killed faster than its parent compound (Table 2), whereas CIC-102 (dihydrochlordene) acted as fast as CIC-103 (dechloro-dihydrochlordene).

In another aspect of this project the minimum effective dose (MED) was examined for 2 pairs of compounds CIC-106/CIC-107 and CIC-126/CIC-127 (dieldrin/dechloro-dieldrin) by using less concentrated solution of the test material, applying the same volume of 1 ml. The original protocols indicate the concentrations as fractions of a percent, e.g. 1/16%, 1/32%, etc. Due to the lack of *Aedes aegypti* mosquitoes, *Culex quinquefaciatus* and *Anopheles quardramaculatus* were used also. The results indicate that the MED of the corresponding derivative seems to be similar or equal to that of the parent compound. No significant differences in the MED in regard to the insecticidal activity were observed. Again, the dechloro derivative CIC-127 (dechloro-dieldrin) at concentrations equal or higher than 39 ppm acts faster against *C. quinquefasciatus* that CIC-126 (dieldrin).

The minimum effective does (MED) of two monodechloro derivatives (CIC-107 and CIC-127) was tested against mosquitoes and found not to be significantly different from the MED of the corresponding parent compounds.

TABLE 3

| Insecticidal Activity of Cyclodienes and their Derivatives Against *Aedes aegypti* | | |
|---|---|---|
| Test Material (1% solution in acetone) | 100% effect[a] in hours | 100 % kill[b] in hours |
| CIC-100 | 1.5 | 3 |
| CIC-101 | 1 | 2.5 |
| CIC-102 | 1 | 5.5 |
| CIC-103 | 1 | 5.5 |
| CIC-106 | 3 | 24 |
| CIC-107 | 2 | 4 |
| CIC-108 | 1.5 | 3 |
| CIC-109 | 1 | 2.5 |
| CIC-110 | 10 | 22 |
| CIC-111 | — | — |
| CIC-116 | 11 | 12 |
| CIC-117 | 1 | 5.75 |
| CIC-118 | 1 | 6.5 |
| CIC-119 | 1.5 | 4 |
| CIC-126 | 2.5 | 5 |
| CIC-127 | 1.5 | 3.5 |
| CIC-128 | .5 | 4 |
| CIC-129 | 1 | 3 |
| CIC-134 (.5%) | 24 | 24 |
| CIC-138 | 0.16 (10 min.) | 9 |
| CIC-139 | 0.16 | 4 |
| CIC-141 | 0.25 | 10 |
| CIC-142 | 0.25 | 3 |
| CIC-143 | 2 | 23 |
| CIC-144 | 0.08 | 23 |
| CIC-145 | 0.08 | 3 |
| CIC-146 | 3 | 24 |
| CIC-147 | 0.08 | 9 |
| CIC-148 | 0.08 | 6 |
| CIC-149 | 0.33 | 9 |
| CIC-150 | 4 | 23 |
| CIC-151 (0.5%) | 0.16 | 12 |
| CIC-158 | 0.08 | 3 |

[a]100% effect in hours = time after which 100% of the mosquitoes were affected, as noted by visual symptoms of a toxic effect such as dead, lying down, wobbly, erratic.
[b]100% kill in hours = time after which 100% of the mosquitoes were killed Further tests were conducted on numerous pests using compounds 142, 145 and 158 (which is a composition made of a mixture of 143, 144, 145 and 148) with results as follows. The compounds killed from 50 to 100% of the larvae of *Aedes aegypti* (mosquito) within 23 hours at a concentration of 100 ppm. In a contact test at 1% concentration the compounds were found to be effective insecticides against:
  Tenebrio molitor (Greater Meal Worm)
  Sitophilus Oryza (Rice Weevil)
  Grainery Weevil (except 142 - no effect)
  Maize Weevil
  Blatella germanica (German cockroach)
  Mosca domestica (House fly)
  Acheta domestica (Crickets) (142 and 158 only mildly effective)
  Cimex lectularius (Bed bugs)
  Ctenocephalides felis (Cat fleas)
  Pediculus humanus (Lice)

In still further contact tests we extended the range of concentration of numerous of the CIC compounds against Aedes aegyptii to determine effect at low concentrations, as illustrated on the following table:

TABLE 3a

Insecticidal Activity of CIC Compounds in the Contact Test (against Aedes aegypti)

| Compound CIC | Percentage of dead after 24 h (±2.5 h) (%) | Concentration of dose (%) |
|---|---|---|
| 101 | 58 | .005 (50 ppm) |
| 103 | 73 (29 h) | .01 |
| 105 | 85 | .0001 |
| 107 | 80 | .005 |
| 109 | 100 | .005 |
| 113 | 95 | .1 |
| 115 | 75 (52 h) | .5 (5000 ppm) |
| 116 | 100 | .05 |
| 117 | 90 | .05 |
| 118 | 83 | .0005 (5 ppm) |
| 119 | 100 | .005 |
| 120 | 100 | .05 (500 ppm) |
| 121 | 95 (32.5 h) | .05 |
| 123 | 85 | .005 |
| 125 | 100 | .001 |
| 127 | 89 | .0005 |
| 129 | 100 | .0005 |
| 130 | 100 | .05 |
| 131 | 100 | .05 |
| 132 | 100 | .05 |
| 133 | 51 | .1 |
| 134 | 88 | .01 |
| 135 | 95 | .0005 |
| 136 | 100 | .005 |
| 137 | 100 | .25 |
| 160 | 71 | .001 |
| 164 | 100 (22 hrs) | .005 |
| 165 | 100 | .0005 |
| 168 | 80 | .001 |

Bioaccumulation and Biodegradation of Dechlorocyclodienes

The experiments described in this section show the difference between the bioaccumulation and biodegradation of the dechloro derivatives of the cyclodienes compared to the corresponding properties of the parent compound. As a model, the rat (Sprague-Dawley) was selected because it is considered to be an acceptable model for man with the present test criteria. The electron-capture (EC) gas chromatography was selected as the analytical method because it is considered the best method for detection of chlorinated compounds if non-radiolabeled test materials are used.

In regard to the possible enviromental exposure, the doses are considered as very high. Oral absorption of 1-10 mg/kg body weight equals a total does of 70-700 mg per 70 kg person, this intake might occur due to accidental ingestion, but not due to exposure in the field, which is much less if the test material is used correctly.

1. Bioaccumulation and Biodegradation of Dieldrin (CIC-126) and Dechloro Dieldrin (CIC-127)

Six female Sprague-Dawley rats (body weights 251-278 g) were dosed orally by means of a stomach tube, 3 animals with CIC-126 (dieldrin), the other 3 received the same amount of CIC-127 (monodechlorodieldrin). The dose was 9.5-10.2 mg test material/kg body weight; the dosing volume 0.6-0.7 ml per animal. 40 mg of the test material was dissolved in 0.5 ml acetone and the solution added to 9.5 ml of 5% CMC in water, resulting in a concentration of 4 mg test material/ml dose solution.

Urine and feces were collected daily for 20 days; on day 20 post-dose the animals were sacrificed and samples from fat, brain, liver, kidney and muscles were taken. All necropsies were without any gross findings; all organs appeared to be in normal condition.

The results of the analysis of the samples taken from selected organs and tissues shows that no CIC-127 could be detected in any organ or tissue after 20 days, whereas after 20 days the concentration of CIC-126 in the fat was in the medium ppm (parts per million) range. The amount of CIC-126 in the fat was 1000 times more than the detection limit of 10 ppb. In other words, the concentrations of this test material differed by a factor of at least 1000. In contrast to CIC-127, CIC-126 was found in low ppm concentrations (liver) or high ppb concentrations (kidney, muscle and brain) after 20 days. Tests indicate fast clearance of the test material CIC-127 and also indicates a low tendency of CIC-127 to be accumulated in the fat. CIC-127 is metabolized rather rapidly, i.e. the accumulation potential of CIC-127 has to be evaluated as much lower than that of CIC-126.

2. Bioaccumulation of CIC-106 - CIC-111 in the Rat

Another three pairs of compounds were tested in the rat: CIC-106 (δ-dihydroheptachlor) and its dechloro analog, CIC-107 (dechloro- δ- dihydroheptachlor); CIC-108 (heptachlor epoxid); and its dechloro analog, CIC-109 (dechloro heptachlor epoxid); and CIC-110 (nonachlor) and its dechloro analog, CIC-111 (dechloro nonachlor).

As the first of this series of experiments, 6 Sprague-Dawley rats (body weight 165-185 g) were orally dosed with CIC-106 and CIC-107 on five consecutive days with a dose of 3 mg test material/kg body weight (total dose 15 mg/kg, dose preparation substantially identical to that described for CIC-126 and CIC-127). Urine and feces were collected daily, food consumption and body weights recorded twice a week (body weights were recorded per animal; all other parameters groupwise. The animals were sacrificed on day 14 of the study (day0: day of first dosing) and samples of liver, kidney, muscle, brain and fat were taken.

Neither CIC-107 nor CIC-106 were found in liver, kidney, brain and muscle. Possible traces of CIC-106 close to the detection limit or below were found in the fat after 15 days, whereas no CIC-107 could be found in the fat. At this dose level the test material stored in fat was too low to determine accurately.

Two additional studies with a total of 9 Sprague-Dawley rats (body weight 190-250 g), 2 for each of the four test materials (CIC-108, CIC-109, CIC-110, and CIC-111) were performed. The oral dose was increased to 5 mg test material/kg body weight on five consecutive days (total dose: 25 mg/kg; dose preparation substantially identical to that of CIC-126 and CIC-127). Body weights were recorded weekly; the animals were sacrificed on day 14 of the study (day 0=day of first dosing), and samples were taken from the fat of the animals.

The animals dosed with CIC-108 and CIC-109 showed no signs of toxicity; the body weights were normal and no abnormal behavior was observed. These findings indicate that CIC-110 and CIC-111 have an acute toxic effect in rats if dosed with 5 mg/kg body weight on five consecutive days (total does: 25 mg/kg). The effects of CIC-111 were stronger than those of CIC-110. Table 4 shows the concentrations of the test materials in the fat of the rats 14 days after the first dose.

The concentrations of CIC-108 and CIC-109 in the fat 14 days after the first of five consecutive doses differ by a factor of 6.3, whereas the amounts of CIC-110 and CIC-111 in the fat after the same period were determined to be approximately the same.

TABLE 4

Concentrations of CIC compounds in the Fat of Rats 14 Days after the first of five Consecutive Doses of 5 mg/kg body weight (total dose: 25 mg/kg).

| Test Material | Animal Number | Concentration in the fat in ppm[a] |
|---|---|---|
| CIC-108 | 108.1 | 70 |
|  | 108.2 | 65 |
| CIC-109 | 109.1 | 11 |
|  | 109.2 | 10.5 |
| CIC-110 | 10.1 | 19 |
|  | 110.2 | 7 |
| CIC-111 | 111.1 | 14 |
|  | 111.2 | 6 |
| CIC-105 | single dose of 29 ppm | 0.3% of applied dose after 24 hrs. |
| CIC-105 | single dose of 23 ppm | 0.4% of applied dose after 48 hrs. |
| CIC-118 | single dose of 24 ppm | 0 after 24 hrs. |
| CIC-118 | single dose of 48 ppm | 0 after 96 hrs. |
| CIC-135 | single dose of 23 ppm | 1.8% of AD in 24 hrs. |

[a] ppm = parts per million

Tests for Insecticidal Activity, Knock-Down Effect and Bioaccumulation

Material and Methods
I. Insecticide Testing
Insects: Mosquitoes
Species: *Aedes aegypti, Anopheles quadramaculatus*

The mosquitoes were bred under controlled conditions (humidity, temperature and nutrition) at White Sands Research center.

Test room temperature: approximately 70° F. (average).
Test room humidity: between 50% and 70% (average).

Procedure:

The test compounds were dissolved in HPLC grade acetone at the appropriate concentrations. One ml of the solution was applied with a disposable 1 ml syringe on filter paper (Whatman 541, 9.0 cm diameter). After evaporation of the acetone, the filter paper was placed in a Petri dish (diameter also about 9.0 cm) with a lid. The lid did not close air tight. The mosquitoes (not less than 5 or more than 20) were transferred in the dish through a hole in the lid. The lid was stopped up with a cotton ball wrapped in filter paper and soaked in sugar water. Two dishes with control insects—the filter paper was treated with 1 ml pure acetone—were observed. Readings were taken 3 to 4 times during the first hour, thereafter every hour.

The insecticide activity was evaluated by the following three criteria:

"Affected" (A)=mosquitoes show abnormal flying behavior or demonstrate hyperactivity.

"Down" (D)=mosquitoes are disabled to fly, lay on their back or side.

"Dead"=mosquitoes are completely moveless (e.g. no movement of body, legs or wints).

these criteria can be considered as very strict.

II. Bioaccumulation Tests in Rats
Species: Sprague Dawley and Fisher Rats
Sex: Female
Age/Weight: Young rats (average weight between 130 and 180 grams)

Procedure

The animals were housed in stainless steel metabolism cages in a temperature controlled animal room. They were quarantined for at least 6 days before being placed on the study. Three rats were taken for each test compound (see appendix for dose levels). Each animal was dosed on five consecutive days by oral gavage. The test compound was dissolved or suspended in 0.5% carboxy methyl cellulose solution or corn oil (Mazola). After 14 days the rats were sacrificed by $CO_2$. Samples of fat (abdominal) liver, kidneys, brain and muscle (leg) were removed and extracted for analysis. The fat of each rat was analyzed separately with regard to the individual total dose. The other organs of all three rats were combined and analyzed with regard to the total dose being applied to all three rats. The analysis was done by gas chromatography under ECD (electron capture detector) detection.

The results of these tests are recorded in Table 5.

TABLE 5

| Compound No. | Name of the Compound | Lowest Concentration for Knockdown | Lowest Concentration With Killing Effect | Bioaccumulation in Rats |
|---|---|---|---|---|
| 138 | 1,2,4,6,7,7-Hexachloro-bicyclo[2.2.1] heptene-2 | 0.25%: 67% down after 10 minutes | 0.125% | 0.08% |
| 139 | 1,2,4,5,7,7-Hexachloro-bicyclo [2.2.1] heptene-2 | 0.25%: 67% down after 10 minutes | 0.125% | 1.14% |
| 141 | 1,4,5,7,7-pentachloro-bicyclo- [2.2.1]-heptene | (5 minutes) 0.5%: 38% down | 0.125% | — |
| 142 | 1,4,7,7-Tetrachloro-bicyclo [2.2.1] -heptene-2 | 0.75%: 37% down after 4 minutes | 0.3% | 1.24% |
| 144 | 1,4,5,6,7-Pentachloro-bicyclo- [2.2.1]-heptane | 0.06%: 55% down | 0.06%: 79% dead after 22 hours | 0.01% |
| 145 | 1,4,5,6,7-Tetrachloro-bicyclo [2.2.1] heptane | 0.08%: 63% down after 5 minutes | 0.04%: 62% dead after 5 hours | >>0.01% |
| 146 | 1,4,5,6,7,7-Hexachloro-bicyclo [2.2.1]-heptane | — | >1% | — |
| 147 | 1,2,4,7,7-Pentachloro- | 0.125%: 63% down | 0.125%: (50% dead | 1.04% |

TABLE 5-continued

| Compound No. | Name of the Compound | Lowest Concentration for Knockdown | Lowest Concentration With Killing Effect | Bioaccumulation in Rats |
|---|---|---|---|---|
| | bicyclo-[2.2.1]-heptene-2 | (10 minutes) | after 1.5 hours) | |
| 148 | 1,4,5,6,7-Pentachloro-bicyclo-[2.2.1]-heptane | 0.06%: 80% | 0.015%: 60% dead after 5 hours | 1.30% (estimate value) |
| 149 | 1,4,7,7-Tetrachloro-bicyclo-[2.2.1]-heptane-poxide (less) | Not very fast knock-down. 0.5%: 36% down after 10 minutes | 0.063%: (67% dead after 6 hours) | — |
| 150 | 1,4,7,7-Tetrachloro-bicyclo [2.2.1]-heptane epoxide | — | 0.5%: 27% dead after 7 hours | — |
| 151 | 1,4,7,7-Tetrachloro-5-methyl-bicyclo [2.2.1]-heptane | 0.5%: 73% down | 0.50%: 73% dead | 0.01% |

METHODS OF USE

The novel bornaphene compounds disclosed above are capable of use by applying an effective amount of the bornaphene to an environment inhabited by the pest for a length of time sufficient to cause the pest to pick up a toxic amount of it. Suitable carriers for the bornaphenes are liquids, solids, semi-solid compositions, and liquid mists or aerosolized compositions. In this manner contact can be made with flying and crawling insects of all kinds. Spraying the compounds into the air is especially effective in view of the highly surprising "knockdown" effect shown by these compounds. The carrier, moreover, should preferably also be one that is not harmful to the environment. Organic liquid carriers such as the known hydrocarbons and organic solvents are usually suitable as carriers and can be made into useful sprays and liquid solutions containing the active compound. Dusts made of finally divided organic or inorganic solid materials upon which the active ingredient and has been adsorbed are also useful dosage forms.

The novel bornaphenes disclosed herein may be used alone or in combination with other biodegradable pesticides or with a bioaccumulable pesticide in relative proportions so that the degree of bioaccumulation of the ultimate composition does not exceed acceptable levels.

While the novel pesticides disclosed above have been presented and described in detail with reference to preferred embodiments, the invention is not intended to be so limited. On the contrary, alternatives, changes or modifications may become apparent to those skilled in the art upon reading the foregoing description. Accordingly, such alternatives, changes and modifications as would occur to a person of ordinary skill in this art are to be consider as forming a part of the instant invention insofar as a fall within the spirit and scope of the attended claims.

I claim:

1. An insecticidal composition characterized by little or no bioaccumulation in the fats or tissues of animals, fowl or fish which comprises an amount effective to kill insects of a compound having the formula

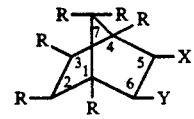

where R is H, Cl or other Hal, hydroxyl, lower alkoxyl, lower alkyl, or cyano; X and Y are H or Hal; and the unsaturated analogs thereof wherein the unsaturation occurs at at least one of the 2 or the 5 positions; with the further proviso that said compound has from 4 to 6 halogens; and a carrier for said compound; said composition being characterized by bioaccumulation of said insecticidal compound not above acceptable limits in animal tissue or fat when said animal is exposed to said insecticide.

2. The composition of claim 1 wherein X is chlorine or H, and Y is chlorine or H.

3. The composition of claim 1 wherein at least one of the R's at position 7 is H.

4. The method of killing insects without causing a resulting undesirable bioaccumulation of insecticide in animal tissue or fat which comprises administering to the insect by contact, oral ingestion or inhalation an amount effective to kill the insect of a composition of the formula shown in claim 1.

* * * * *